United States Patent
Hulme

Patent Number: 5,493,405
Date of Patent: Feb. 20, 1996

[54] SPECTROPHOTOMETER CELL HAVING AN INTERMEDIATE WALL MEMBER AND AN INTEGRAL LENS

[75] Inventor: Keith Hulme, Hainault, Great Britain

[73] Assignee: Optiglass Limited, Hainault, United Kingdom

[21] Appl. No.: 277,068

[22] Filed: Jul. 19, 1994

[30] Foreign Application Priority Data

Jul. 19, 1993 [GB] United Kingdom ............. 9314926

[51] Int. Cl.$^6$ .......................... G01N 1/10; G01N 21/00
[52] U.S. Cl. .................. 356/440; 356/246; 250/576
[58] Field of Search .............. 250/576; 356/440, 356/246

[56] References Cited

U.S. PATENT DOCUMENTS

| | | | |
|---|---|---|---|
| 2,562,181 | 7/1951 | Frommer | 356/440 |
| 2,732,753 | 1/1956 | O'Kouski | 250/576 |
| 2,810,315 | 10/1957 | Miller | 250/576 |
| 3,551,062 | 12/1970 | Brown | 250/576 |
| 3,560,077 | 2/1971 | Sooy et al. | 356/246 |
| 3,573,470 | 4/1971 | Haley | 356/246 |
| 3,941,487 | 3/1976 | Ehret et al. | 356/246 |
| 4,619,530 | 10/1986 | Meserol et al. | 356/246 |
| 4,825,076 | 4/1989 | Shields | 250/343 |
| 4,827,143 | 5/1989 | Munakata et al. | 356/339 |
| 4,872,753 | 10/1989 | Danigel et al. | 356/246 |
| 4,886,356 | 12/1989 | Paradis | 356/440 |
| 5,037,199 | 8/1991 | Hlousek | 356/246 |
| 5,104,218 | 4/1992 | Garner | 250/576 |
| 5,331,409 | 7/1994 | Thurtell et al. | 356/440 |

FOREIGN PATENT DOCUMENTS

| | | |
|---|---|---|
| 0422448A2 | 4/1991 | European Pat. Off. . |
| 1347827 | 2/1974 | United Kingdom . |
| 2162961 | 2/1986 | United Kingdom . |

*Primary Examiner*—Frank Gonzalez
*Assistant Examiner*—Jason D. Eisenberg
*Attorney, Agent, or Firm*—Evenson, McKeown, Edwards & Lenahan

[57] ABSTRACT

A cell for measuring the spectrum of a sample in a light beam of a spectrophotometer, comprises an incident wall member 17 and an exit wall member 15 spaced therefrom to define therebetween a sample chamber 14 extending between internal faces of the internal and exit wall members, the incident wall member including a window 18 with a lens 19 adapted to concentrate the light beam incident thereon into the sample chamber 14.

12 Claims, 4 Drawing Sheets

SPECTROPHOTOMETER CELL HAVING AN INTERMEDIATE WALL MEMBER AND AN INTEGRAL LENS

SUMMARY OF THE INVENTION

The present invention relates to a cell for measuring the spectrum of a sample, particularly but not exclusively a fluid sample, in a light beam of a spectrophotometer, comprising an incident wall member and an exit wall member spaced therefrom to define therebetween a sample chamber extending between the internal faces of the wall members, each wall member including a window adjacent the respective end of the sample chamber to enable an external light beam to pass through the chamber.

Such cells are typically produced from at least two pieces of polished optical material. The pieces are joined by the use of heat alone. Thus, in this technique, there are no intermediate or adhesive materials used in the construction of cells, with the result that they are completely homogeneous and permanently resistant to all solutions other than those which attack the raw materials. During the production process any strain in the cell is removed by careful annealing. Thus the cells can withstand a reasonable amount of physical and thermal shock as well as ultrasonic vibration and pressure differentials of up to several atmospheres. With care, the cells may even be used at high and low temperatures. In certain circumstances where dissimilar materials are used it is also known to use a glue, adhesive, or other materials to bond the windows to the cell.

It is possible that cells are made from different raw materials depending on their suitability for any given application. For example, the cells may be made from, glass, quartz or even certain plastics, such as acrylics. The type of material end cell used will depend on the particular use of the cell. The cells may be used in many different types of photometry, such as spectrophotometers, fluorimeters, colorimeters, absorptiometers and in detectors for high pressure liquid chromatography. In this specification, the term light is used to mean the relevant range of electromagnetic radiation for the particular type of measurement being made, not merely visible wavelengths.

Cells come in a variety of different types, for the various different types of spectrometry. In most circumstances the external dimensions of the cell are dictated by the instrument cell holders presently used. Reference is made to a document issued by Starna Ltd. of Romford, Essex, entitled "Starna Spectrophotometer Cells" first published in 1977, which describes a range of the most commonly used spectrophotometer cells.

While the above described cells which work adequately for applications where the sample chamber volume is approximately between 50 to 500 μL (50 to 500×10$^{-9}$M$^3$), it is increasingly necessary to make the sample chamber smaller in volume, especially in microbiological fields. Often, it is necessary to have a sample chamber volume of 5 μL or less. A particular advantage of a smaller volume is that it is possible to pass more samples through the chamber for analysis in a given time which has significant commercial cost advantages. However, as the sample chamber becomes smaller in cross section, the amount of light passing through the sample falls.

Consequently, the fall in the amount of energy reduces the signal to noise ratio and may reach a level at which reliable measurements are impossible to make.

It has been suggested to focus the light source of the spectrophotometer onto a smaller sample chamber. This is difficult as the sample chambers have a typical cross-section of only 1×1 mm (1×10$^{-6}$M$^2$) and normally spectrophotometer lenses have a focal length of between 30 mm and 200 mm. Thus, only a small misalignment of the cell in the spectrophotometer may cause the light beam to completely miss the sample chamber. In practice, this is difficult and expensive to avoid. Further, this has another disadvantage that the spectrophotometer is limited when used with longer path length cells as the narrow beam needed would reduce its performance as it would only pass through a small fraction of the available aperture.

The present invention seeks to provide a spectrophotometer cell with improved light throughput so that satisfactory measurements can be made with smaller volumes of sample, thereby not requiring a dedicated spectrophotometer.

According to the present invention, a cell for measuring the spectrum of a sample in a light beam of a spectrophotometer, comprising an incident wall member and an exit wall member spaced therefrom to define therebetween a sample chamber extending between internal faces of the internal and exit wall members, the incident wall member including a window to enable the light beam to enter the sample chamber, wherein the cell includes a lens in the light beam path adapted to concentrate the light beam incident thereon into the sample chamber.

By incorporating the lens in the cell, the light can be concentrated on the sample to improve light throughput and produce a distinct measurable spectrum. This means that it is not necessary to specially adapt the spectrophotometer for use with a particularly shall sample. The light beam is refocused by the lens in the cell and so allows the use of a standard spectrophotometer. Of course, there is no reason why the cells of the present invention cannot be used with sample chambers of other sizes, to improve the amount of light that passes correctly through a particular sample where dimensional details so allow.

In a preferred embodiment the lens concentrates the light onto a point midway in the sample chamber.

Preferably, a further lens is incorporated in the exit wall member, the further lens being adapted to diverge light from the sample chamber on to a measuring device.

In another embodiment, an intermediate wall member is located between the incident wall member and the exit wall member, the sample chamber being defined between the intermediate wall member and the exit wall member. In this embodiment, a further lens may be incorporated in the intermediate wall member to, modify the focussing of the beam. Preferably, the beam focus is modified to form a substantially parallel light beam through the sample chamber.

BRIEF DESCRIPTION OF THE DRAWINGS

Embodiments of the invention will now be described with reference to the accompanying drawings, in which.

DETAILED DESCRIPTION OF THE DRAWINGS

Figure 1A:
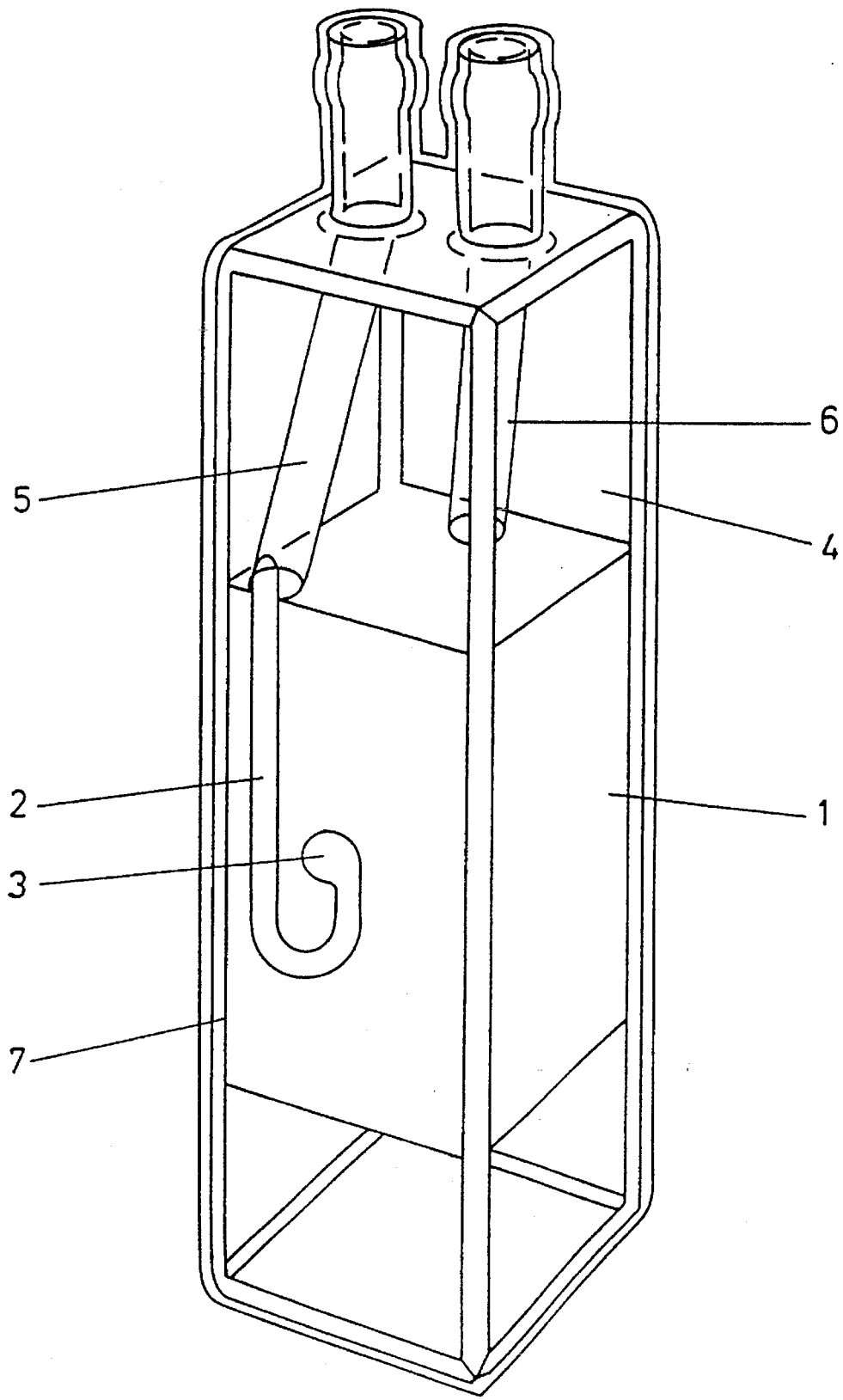
FIG. 1a shows a known flow through spectrophotometer cell.

FIG. 1a shows a typical flow through cell which would normally be constructed from a number of pieces of homogeneous and optically suitable materials such as Quartz, Glass, or Acrylic which have been fused or otherwise bonded together. Inlet/Outlet tubes or ducts are formed in the cell by conventional or ultrasonic machining or drilling. The example shown comprises a rectangular block of black-quartz 1 which has a j-shaped channel 2 formed in one side face by ultrasonic machining. A sampling chamber 3 is formed by machining a bore through the block from the end of the channel 2 perpendicular to the face in which the channel 2 is formed.

A transparent block of quartz 4 is fused to the top of the block 1. Prior to this joining step, an inlet duct 5 is drilled ultrasonically in the block 4 so as to be aligned with the channel 2 and a similarly drilled outlet duct 6 is also provided. The outlet duct 6 is aligned with a bore (not shown) in the block 4 which leads to the end of the chamber 3 remote from the channel 2 to thereby complete the fluid flow path through the chamber 2. The channel 2 and the inlet to the chamber 3 are closed by a transparent quartz sheet 7 which is fused to the outside face of the block 1 to form the inlet passage to the chamber for the liquid to be sampled.

Figure 1B:
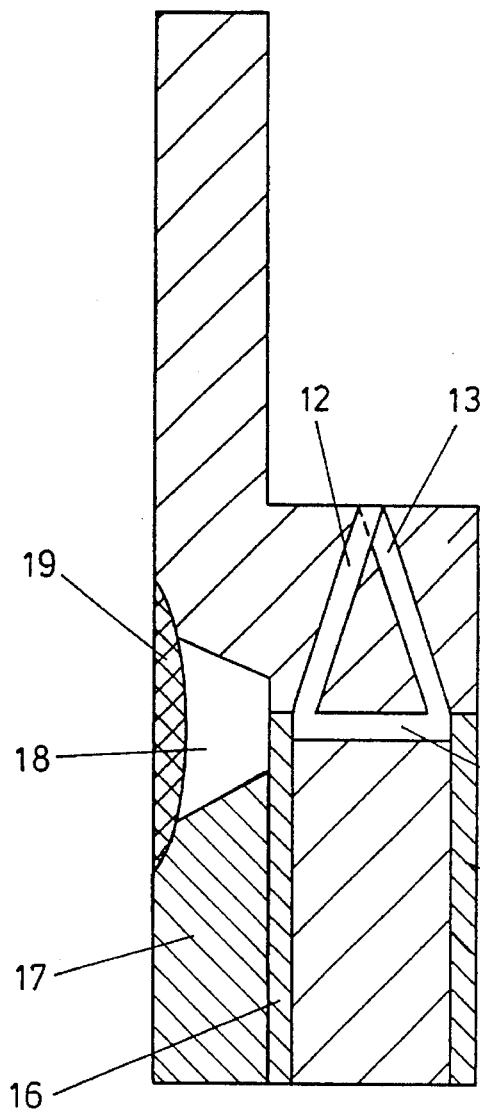
FIGS. 1b and 1c show spectrophotometer cells according to the present invention.
Figure 1C:
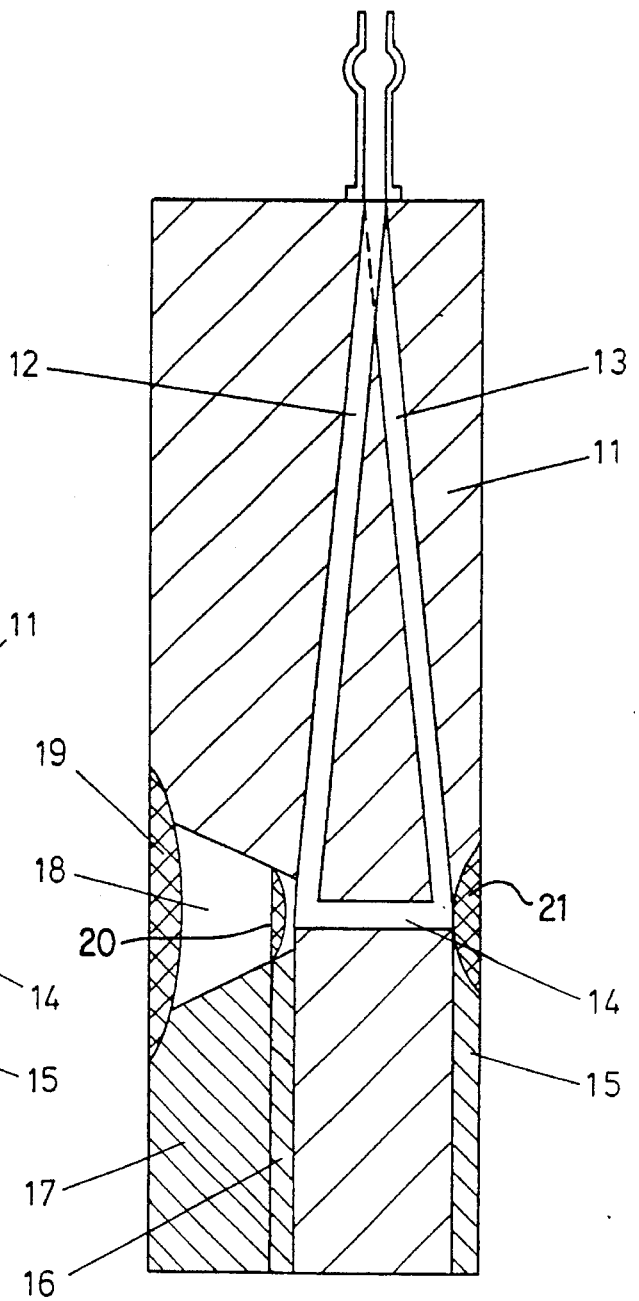

FIGS. 1b and 1c show two embodiments of the present invention in which like parts bear like references. The cell is constructed of a number of components formed of quartz, which are fused together to form the complete cell. In a top face of a first block of black quartz 11, inlet and outlet ports 12 and 13 are formed by ultrasonic drilling. At the top face the ports are aligned in a plane normal to the paper and are inclined at an angle to respective ends of a sampling chamber 14. The sampling chamber 14 is drilled ultrasonically through the quartz and the ends of the bore are closed by respective transparent quartz sheets 15, 16 which are fused to the faces of the black block 11 to complete the chamber 14 and to provide windows into the chamber so that a light beam can pass through the chamber. The inlet/outlet ports 12, 13 may be manufactured to receive hypodermic needles or pipette tips to inject or withdraw the sample material.

A further block of black quartz 17 is fused to the block 11 and sheet 16. Prior to fusing, the block 17 has a tapered bore 18 drilled therein so as to be aligned with the axis of the chamber 14. The outer end of the bore 18 is closed by a lens 19 fused or otherwise bonded to the block 17 to form an incident wall. The lens 19 serves to focus the light beam at a point adjacent the middle of the chamber 14.

It is of course possible for the lens 19 to be formed in the sheet 16 or be bonded thereto to perform both the function of a lens and a closure member for the end of the chamber 14.

Figure 2:
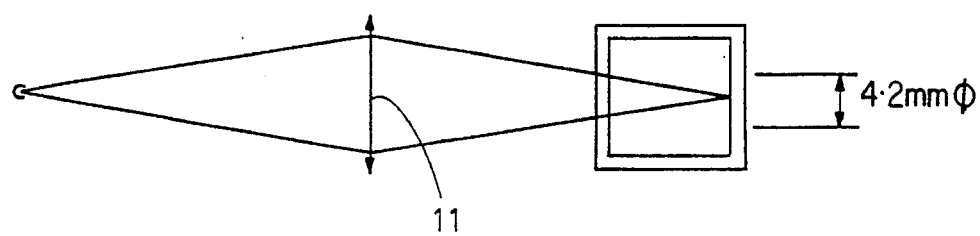
FIG. 2 shows a known cell in a light source of a spectrophotometer.

FIG. 2 shows a cell mounted in the cell so that the light is focused by the instrument optics through the entrance to the sample chamber onto the exit wall, but the instrument optics could be so designed to focus the light in the middle of the sample chamber, or elsewhere as desired, by choosing the appropriate lens and ensuring accurate positioning of the cell in the spectrophotometer. The black cell walls stop transmission of any light except light directed by the lens through the sample chamber, thereby increasing the resolution of the measured spectrum.

Figure 3A:
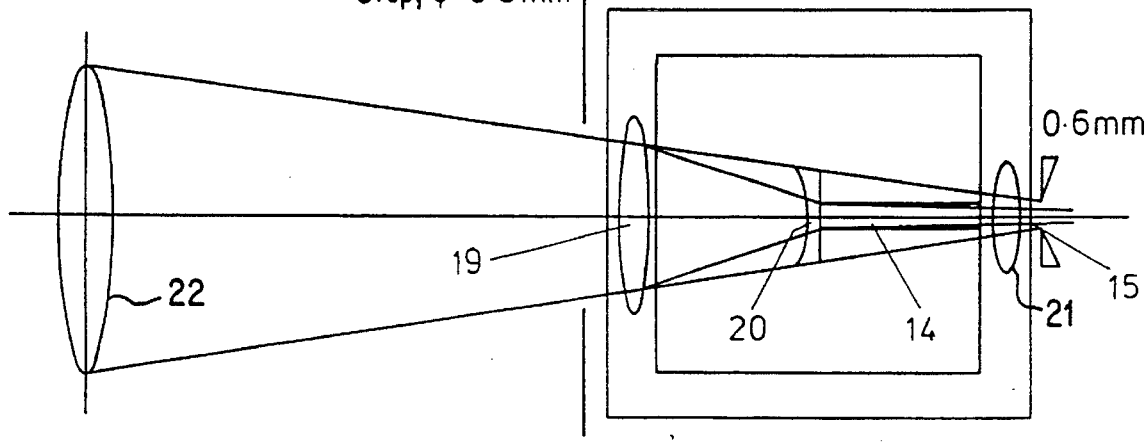
FIG. 3a and 3b shows schematically a cell of the present invention in a light source of a spectrophotometer.
Figure 3B:
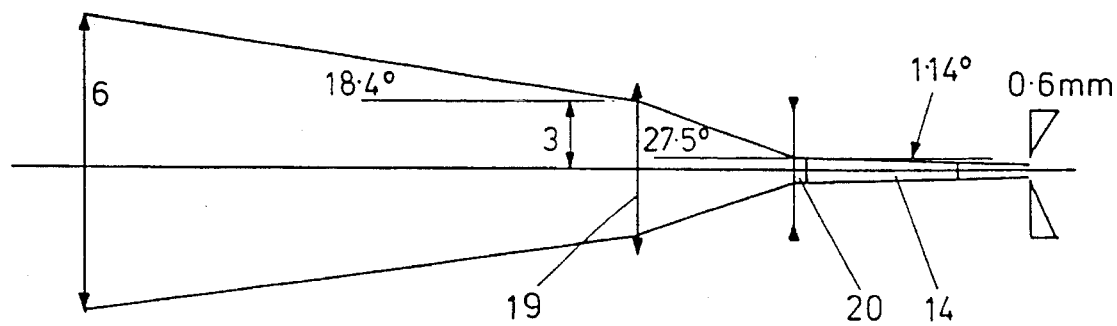

As shown schematically in FIGS. 1c and 3a, in a further embodiment of the present invention, a further lens 20 is incorporated in an intermediate wall formed by the sheet 16. As shown, the main instrument lens 22 serves to direct the light beam from the lens 19 in the incident wall which refocusses the beam onto the lens 20. The further lens 20 is adapted to direct the beam through the sampling chamber in as near a parallel beam as possible. In this way, the maximum amount of beam energy is concentrated in the chamber.

The exit wall 15 may also include a further lens 21 or reflector system to direct the beam exiting from the sample chamber onto the detector. In cells for use in a fluorimeter, an additional window would be provided in the side walls of the sample chamber.

Figure 4:
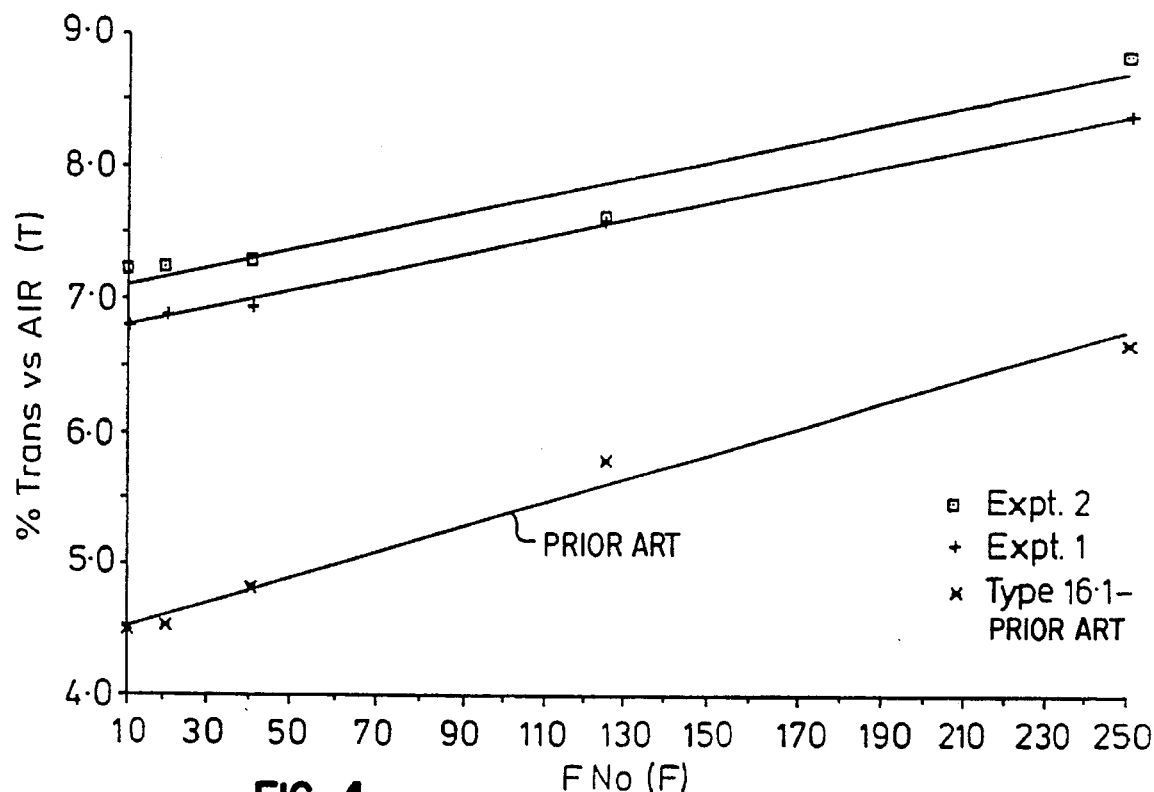
FIG. 4 shows a graph of the transmission percentage compared to air results of the known cell and cells according to the present invention.
Figure 5:
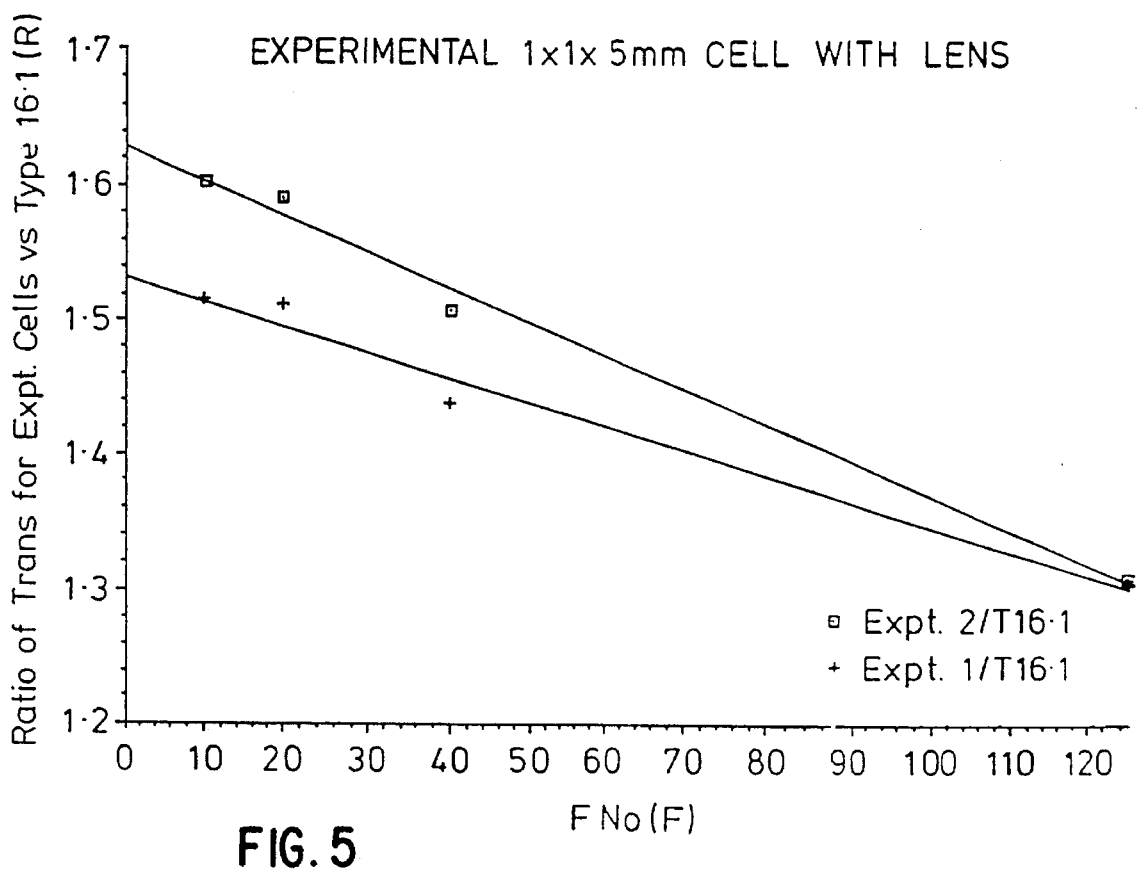
FIG. 5 shows a graph of the transmission ratio compared to air for the known cell and cells according to the present invention.

A cell according to the present invention was tested in the following manner:
Procedure:

The cells were tested for light throughput at a variety of apertures using the AA6 spectrophotometer at a wavelength of 250 nm. A dye solution was also used to check the measurement accuracy of the cells, with the instrument operating at F40 at a wavelength of 594.5 nm. All measurements were made with a spectral band width of 0.5 nm and a slit height of 1 mm. A hydrogen lamp was used as the 250 nm source and an iron lamp as the 594.4 nm source.
Results:

The results of the light through put experiments are illustrated on the accompanying graphs, comprising FIGS. 4 and 5. The measurement accuracy experiment was satisfactory, the mean reading in the experimental cells was 0.179 against a figure of 0.361 for the same solution measured in a standard Type 1 Quartz 10 mm cell. The experimental cell had a better light through put than the conventional Type 16.10 cell with a 10 µl sample chamber of cross section of 1×1 mm and the advantage increased at lower F numbers, however the AA6 can not be operated below F10, so the degree of improvement at low F numbers is difficult to estimate.

The following information is a guide to the practical useable range covered by often used materials:
1) Optical Glass 334 nm through to 2500 nm.
2) Treated Optical Glass 300 nm through to 2600 nm.
3) Near UV Silica Quartz material suitable between 210 nm and 2700 nm. Not generally recommended for Fluorescence work.
4) Far UV Silica Quartz material suitable between 170 nm and 2600 nm. They show no fluorescence, but do have a strong absorption band at 2700 nm.
5) IR Silica Quartz material with no significant absorption band in the UV is suitable between 220 nm to 3800 nm.

Cells constructed according to the present invention have the advantage that satisfactory readings can be obtained with much smaller samples. This not only increases the versatility of the spectrophotometer, but can also substantially increase the rate of testing samples with a consequent increase in productivity.

I claim:

1. A cell for measuring a spectrum of a sample in a light beam of a spectrophotometer, said cell comprising:
   a substantially solid unitary member having an incident wall surface in a spaced relationship to an exit wall surface;
   an intermediate wall member arranged between the incident wall surface and the exit wall surface;

a sample chamber extending through the unitary member and defined between the intermediate wall member and the exit wall surface;

at least one window adjacent the sample chamber arranged to enable the light beam to pass through the sample chamber; and a lens fixed with and incorporated in the unitary member and arranged to focus the light beam into the sample chamber.

2. The cell according to claim 1, wherein the unitary member comprises at least one substantially solid block member.

3. The cell according to claim 1, wherein said lens is incorporated in the incident wall surface.

4. The cell according to claim 1, wherein said lens is bonded or fused to said incident wall surface.

5. The cell according to claim 1, wherein an exit lens is incorporated in the exit wall surface, the exit lens arranged to direct light from the sample chamber onto a measuring device.

6. The cell according to claim 1, wherein a further-lens is incorporated in the intermediate wall member to modify the focussing of the light beam.

7. The cell according to claim 6, wherein the further lens is arranged to modify the focussing of the beam so as to form a substantially parallel light beam through the sample chamber.

8. A cell according to claim 6, wherein an exit lens is incorporated in the exit wall surface, the exit lens being arranged to direct light from the sample chamber onto a measuring device.

9. The cell according to claim 1, wherein the sample chamber has a volume of less than 50 μL.

10. The cell according to claim 1, wherein the sample chamber has a volume of less than 5 μL.

11. A cell according to claim 1, wherein the lens concentrates the light beam onto a point midway in the sample chamber.

12. A cell according to claim 1, wherein the exit wall surface includes a deflector or lens system to direct the light beam exiting the sampling chamber on to a detector means.

* * * * *